United States Patent
Ogiwara

(10) Patent No.: US 9,157,078 B2
(45) Date of Patent: Oct. 13, 2015

(54) CELL-ADHESIVE PROTEIN

(71) Applicant: FUJIFILM Corporation, Minato-Ku, Tokyo (JP)

(72) Inventor: Kazutaka Ogiwara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/039,910

(22) Filed: Sep. 27, 2013

(65) Prior Publication Data

US 2014/0094590 A1 Apr. 3, 2014

Related U.S. Application Data

(63) Continuation of application No. PCT/JP2012/058296, filed on Mar. 29, 2012.

(30) Foreign Application Priority Data

Mar. 30, 2011 (JP) .................................. 2011-074833

(51) Int. Cl.
 C07K 14/78 (2006.01)
 C12N 11/02 (2006.01)
(52) U.S. Cl.
 CPC ................ *C12N 11/02* (2013.01); *C07K 14/78* (2013.01)
(58) Field of Classification Search
 CPC ...................................................... C07K 14/78
 USPC .......................................................... 530/354
 See application file for complete search history.

(56) References Cited

U.S. PATENT DOCUMENTS

| | | | |
|---|---|---|---|
| 2010/0029885 A1 | 2/2010 | Van Kessel | |
| 2010/0119574 A1 | 5/2010 | De Boer et al. | |
| 2012/0165263 A1 | 6/2012 | Hiratsuka et al. | |

FOREIGN PATENT DOCUMENTS

| | | | |
|---|---|---|---|
| JP | 2002-509893 A | 4/2002 | |
| JP | 2009-520503 A | 5/2009 | |
| JP | 2009-535445 A | 10/2009 | |
| JP | 2010-503613 A | 2/2010 | |
| JP | 2010-519251 A | 6/2010 | |
| WO | 99/49883 A1 | 10/1999 | |
| WO | 01/77349 A1 | 10/2001 | |
| WO | 2007/076032 A2 | 7/2007 | |
| WO | 2007/076354 A2 | 7/2007 | |
| WO | 2007/126314 A1 | 11/2007 | |
| WO | 2008/009085 A1 | 1/2008 | |
| WO | 2008/103041 A1 | 8/2008 | |
| WO | 2008/103042 | * | 8/2008 |
| WO | WO 2008103041 | * | 8/2008 |
| WO | 2009/044407 A1 | 4/2009 | |
| WO | WO 2009044407 | * | 4/2009 |
| WO | 2011/027850 A1 | 3/2011 | |

OTHER PUBLICATIONS

International Preliminary Examination Report on Patentability for PCT/JP2012/058296 dated Oct. 10, 2013, with English Translation.
Communication dated Oct. 13, 2014, issued by the European Patent Office in counterpart EP Application No. 12764658.
Miles et al., "Functional Methionines in the collagen/gelatin binding domain of plasma fibronectin: Effects of Chemical Modification by Chloramine T", Biochemistry 32:8168-8178 (1993).
Notification of the First Action for Chinese Application No. 201280015848.0 dated Sep. 2, 2014.
Yan et al., "Amino Acid Analysis in Oxidative Product of the Gelatin", The Science and Technology of Gelatin, 15(2):68-81 (1995).
Office Action for Japanese Application No. 2011-74833 dated Oct. 14, 2014.
Sadako Tani et al., "Oxidation of Methionine in Gelatin", The Journal of the Society of Scientific Photography in Japan 1995, pp. 19-24, vol. 58, No. 1.
Shinya Takahashi et al., "Physical and Chemical Changes of Gelatins by Oxidation Treatment", The Journal of Scientific Photography 1988, pp. 22-28, vol. 51, No. 1.
Jeffrey W. Finch et al., "Mass Spectrometric Identification of Modifications to Human Serum Albumin Treated with Hydrogen Peroxide", Archives of Biochemistry and Biophysics, Sep. 1993, pp. 595-599, vol. 305, No. 2.
International Search Report for PCT/JP2012/058296 dated Jun. 19, 2012.
Written Opinion for PCT/JP2012/058296 dated Jun. 19, 2012.
Communication dated May 7, 2015 from the State Intellectual Property Office of the People's Republic of China in counterpart application No. 201280015848.0.

* cited by examiner

*Primary Examiner* — Karen Cochrane Carlson
(74) *Attorney, Agent, or Firm* — Sughrue Mion, PLLC

(57) ABSTRACT

It is an object of the present invention to provide a protein having high cellular adhesiveness that is useful as a cell adhesion support. The present invention provides a cell-adhesive protein comprising methionine, wherein at least a portion of the methionine residues is oxidized.

16 Claims, 1 Drawing Sheet

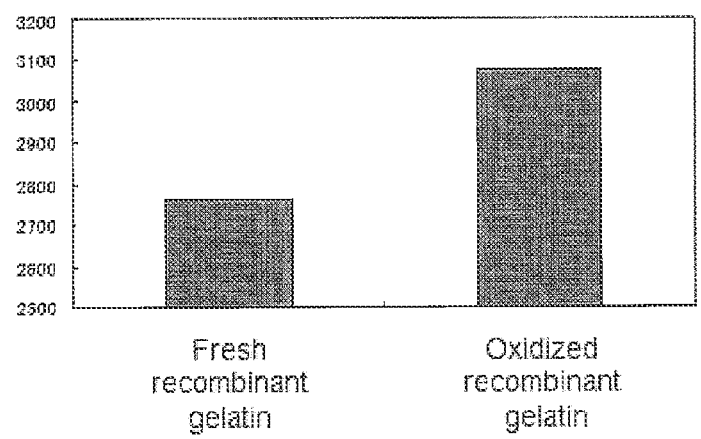

SEQUENCE LISTING

<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: recombinant

<400> SEQUENCE: 1

```
Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
        275                 280                 285

Gly Ala Ala Gly Leu Pro Gly Pro Lys Gly Glu Arg Gly Asp Ala Gly
    290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350
```

```
Pro Lys Gly Glu Arg Gly Asp Ala Gly Pro Lys Gly Ala Asp Gly Ala
        355                 360                 365
Pro Gly Lys Asp Gly Val Arg Gly Leu Ala Gly Pro Pro Gly Ala Pro
    370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
            420                 425                 430
Gly Glu Arg Gly Ala Ala Gly Leu Pro Gly Pro Lys Gly Glu Arg Gly
            435                 440                 445
Asp Ala Gly Pro Lys Gly Ala Asp Gly Ala Pro Gly Lys Asp Gly Val
        450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
            500                 505                 510
Ile Gly Pro Pro Gly Pro Ala Gly Ala Pro Gly Ala Pro Gly Leu Gln
            515                 520                 525
Gly Met Pro Gly Glu Arg Gly Ala Ala Gly Leu Pro Gly Pro Lys Gly
            530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: recombinant

<400> SEQUENCE: 2

Asp Arg Gly Asp
1

<210> SEQ ID NO 3
<211> LENGTH: 4
<212> TYPE: PRT
<213> ORGANISM: Artificial Sequence
<220> FEATURE:
<223> OTHER INFORMATION: recombinant

<400> SEQUENCE: 3

Arg Glu Asp Val
1

<210> SEQ ID NO 4
<211> LENGTH: 5
<212> TYPE: PRT
<213> ORGANISM: Artificial Sequence
<220> FEATURE:
<223> OTHER INFORMATION: recombinant
```

```
<400> SEQUENCE: 4

Tyr Ile Gly Ser Arg
1               5

<210> SEQ ID NO 5
<211> LENGTH: 5
<212> TYPE: PRT
<213> ORGANISM: Artificial Sequence
<220> FEATURE:
<223> OTHER INFORMATION: recombinant

<400> SEQUENCE: 5

Pro Asp Ser Gly Arg
1               5

<210> SEQ ID NO 6
<211> LENGTH: 7
<212> TYPE: PRT
<213> ORGANISM: Artificial Sequence
<220> FEATURE:
<223> OTHER INFORMATION: recombinant

<400> SEQUENCE: 6

Arg Tyr Val Val Leu Pro Arg
1               5

<210> SEQ ID NO 7
<211> LENGTH: 6
<212> TYPE: PRT
<213> ORGANISM: Artificial Sequence
<220> FEATURE:
<223> OTHER INFORMATION: recombinant

<400> SEQUENCE: 7

Leu Gly Thr Ile Pro Gly
1               5

<210> SEQ ID NO 8
<211> LENGTH: 10
<212> TYPE: PRT
<213> ORGANISM: Artificial Sequence
<220> FEATURE:
<223> OTHER INFORMATION: recombinant

<400> SEQUENCE: 8

Arg Asn Ile Ala Glu Ile Ile Lys Asp Ile
1               5                   10

<210> SEQ ID NO 9
<211> LENGTH: 5
<212> TYPE: PRT
<213> ORGANISM: Artificial Sequence
<220> FEATURE:
<223> OTHER INFORMATION: recombinant

<400> SEQUENCE: 9

Ile Lys Val Ala Val
1               5

<210> SEQ ID NO 10
<211> LENGTH: 4
<212> TYPE: PRT
<213> ORGANISM: Artificial Sequence
<220> FEATURE:
<223> OTHER INFORMATION: recombinant
```

```
<400> SEQUENCE: 10

Asp Gly Glu Ala
1

<210> SEQ ID NO 11
<211> LENGTH: 4
<212> TYPE: PRT
<213> ORGANISM: Artificial Sequence
<220> FEATURE:
<223> OTHER INFORMATION: recombinant

<400> SEQUENCE: 11

Glu Arg Gly Asp
1
```

CELL-ADHESIVE PROTEIN

TECHNICAL FIELD

The present invention relates to a protein having high cellular adhesiveness in which at least a portion of methionine residues is oxidized, and a cell adhesion substrate using the same.

BACKGROUND ART

In recent years, clinical studies regarding cell transplantation using stem cells have been vigorously carried out. Treatments such as peripheral vessel regeneration have been progressed using marrow monocytes or vascular endothelial progenitor cells. However, it has become clear that, after transplantation of cells, the transplanted cells engrafted into tissues at an extremely low survival rate, and this is considered problematic. Thus, an attempt to increase the survival rate or engrafted rate of the transplanted cells has been made by mixing a base material to which cells adhere, such as an extracellular matrix, with the cells to be transplanted, and then transplanting the thus obtained mixture. For instance, studies have been conducted to transplant mesenchymal cells together with a base material so as to treat cartilage. However, a majority of the studies have been at an animal experiment level. To date, there have been no reports providing revolutionary results.

Meanwhile, an amino acid, cysteine, has been known as a representative protecting group for protein oxidation. Cysteine has a free highly reactive SH group, and this SH group functions as a scavenger or reservoir for radicals and the like. In addition to such cysteine, methionine is also considered as an essential amino acid fur oxidative stress. There has been a report regarding methionine oxidation in proteins, demonstrating that methionine functions as an antioxidant amino acid (Non Patent Document 1).

Peptides or proteins comprising the oxidized methionine are described, for example, in Patent Documents 1 to 3. Patent Document 1 describes a synthetic cyclic peptide having a specific consensus sequence, in which a methionine residue is substituted with an oxidized methionine residue. Patent Document 2 describes a pharmaceutical product comprising thymosin β4, in which the methionine residue that is the 6$^{th}$ amino acid from the N-terminus is oxidized to methionine sulfoxide. Patent Document 3 describes a composition comprising a CTLA4-Ig molecule, in which approximately 2.5% or less of the cytotoxic T-lymphocyte antigen 4 (CTLA4)-Ig molecule is oxidized. However, none of the above-mentioned peptides or proteins has cellular adhesiveness.

Gelatin has been well known as a representative scaffolding material used in the field of regenerative medicine as a whole. Gelatin has been known as a highly biocompatible and highly safe material, and thus, it has been frequently applied for medical use. Also, collagen has been known as a proven material. However, collagen has solubility lower than that of gelatin, and it is highly restricted by the concentration and pH of a solution thereof (that is to say, collagen cannot be used to prepare a neutral solution of collagen having a high concentration of several tens of percent, etc.). Hence, products processable, producible, or moldable from collagen are generally limited. Accordingly, it has been desired to develop a scaffolding base material with improved cellular adhesiveness, which comprises gelatin.

PRIOR ART DOCUMENTS

Patent Documents

Patent Document 1: JP Patent Publication (Kohyo) No. 2010-503613 A
Patent Document 2: JP Patent Publication (Kohyo) No. 2002-509893 A
Patent Document 3: JP Patent Publication (Kohyo) No. 2009-520503 A

Non Patent Documents

Non Patent Document 1: Finch et. al.: Arch. Biochem. Biophys. 305, 1993, 595-599

SUMMARY OF INVENTION

Object to be Solved by the Invention

It is an object of the present invention to solve the above-mentioned problems of the prior art techniques. Specifically, it is an object of the present invention to provide a protein having high cellular adhesiveness that is useful as a cell adhesion support. It is a particular object of the present invention to provide a cell-adhesive protein whose cellular adhesiveness has been improved by factors other than cell adhesion sequence, and a cell adhesion support comprising the same.

Means for Solving the Object

As a result of intensive studies directed towards achieving the above-mentioned objects, the present inventors have found that a recombinant gelatin having an amino acid sequence derived from a partial amino acid sequence of collagen, in which methionine has been oxidized, has a higher cell adhesion rate than that of a gelatin in which the degree of oxidation of methionine is low. The present invention has been completed based on these findings.

Thus, the present invention provides a cell-adhesive protein comprising methionine, wherein at least a portion of methionine residues is oxidized.

Preferably, 7% or more of the methionine residues in the protein is oxidized.

Preferably, at least a portion of the methionine residues is oxidized by an oxidizing agent.

Preferably, the cellular adhesiveness is improved by oxidization of the methionine residue.

Preferably, the cell-adhesive protein is a gelatin-like protein.

Preferably, the gelatin-like protein is gelatin, collagen, fibronectin, pronectin, vitronectin, or a combination thereof.

Preferably, the gelatin-like protein is a recombinant gelatin having an amino acid sequence derived from a partial amino acid sequence of collagen.

Preferably, the recombinant gelatin has repeats of a sequence represented by Gly-X-Y (wherein X and Y each independently represent any amino acid) that is characteristic to collagen (wherein a plurality of sequences Gly-X-Y may be identical to or different from one another), and has a molecular weight of 2 KDa or more and 100 KDa or less.

Preferably, the recombinant gelatin has repeats of a sequence represented by Gly-X-Y (wherein X and Y each independently represent any amino acid) that is characteristic to collagen (wherein a plurality of sequences Gly-X-Y may be identical to or different from one another), and has a molecular weight of 10 KDa or more and 90 KDa or less.

Preferably, the recombinant gelatin has repeats of a sequence represented by Gly-X-Y (wherein X and Y each independently represent any amino acid) that is characteristic to collagen (wherein a plurality of sequences Gly-X-Y may be identical to or different from one another), and comprises two or more sequences of cell adhesion signals in a single molecule thereof.

Preferably, the cell adhesion signal is an amino acid sequence represented by Arg-Gly-Asp.

Preferably, the amino acid sequence of the recombinant gelatin does not comprise any of serine and threonine.

Preferably, the amino acid sequence of the recombinant gelatin does not comprise any of serine, threonine, asparagine, tyrosine, and cysteine.

Preferably, the amino acid sequence of the recombinant gelatin does not comprise an amino acid sequence represented by Asp-Arg-Gly-Asp (SEQ ID NO: 2).

Preferably, the recombinant gelatin is represented by the following formula:

A-[(Gly-X-Y)$_n$]$_m$-B wherein A represents any given amino acid or amino acid sequence, B represents any given amino acid or amino acid sequence, an n number of X each independently represent any amino acid, an n number of Y each independently represent any amino acid, n represents an integer of 3 to 100, m represents an integer of 2 to 10, and an n number of Gly-X-Y may be identical to or different from one another.

Preferably, the recombinant gelatin is represented the following formula:

Gly-Ala-Pro-[(Gly-X-Y)$_{63}$]$_3$-Gly wherein 63 X each independently represent any amino acid, 63 Y each independently represent any amino acid, and an n number of Gly-X-Y may be identical to or different from one another.

Preferably, the recombinant gelatin has (1) the amino acid sequence shown in SEQ ID NO: 1, or (2) an amino acid sequence having homology of 80% or more with the amino acid sequence shown in SEQ ID NO: 1 and having cellular adhesiveness.

Preferably, the recombinant gelatin is cross-linked.

Preferably, the cross-linking is carried out with an aldehyde, a condensing agent, thermal photocrosslinking, or an enzyme.

The present invention further provides a cell adhesion support comprising the cell-adhesive protein of the present invention as mentioned above.

The present invention further provides a method for producing the cell-adhesive protein of the present invention as mentioned above, which comprises treating a cell-adhesive protein comprising methionine with an oxidizing agent.

Effect of the Invention

The cell-adhesive protein according to the present invention wherein at least a portion of methionine residues is oxidized, has an improved cell adhesion rate than that of a cell-adhesive protein wherein methionine is not oxidized. A cell adhesion support comprising the cell-adhesive protein of the present invention has high cellular adhesiveness. Accordingly, cells can be stably supplied into a living body by allowing this cell adhesion support to retain the cells and then administering the cell adhesion support into the living body.

BRIEF DESCRIPTION OF THE DRAWINGS

FIG. 1 shows the results obtained by measuring the cellular adhesiveness of a recombinant gelatin immediately after preparation and an oxidized recombinant gelatin.

EMBODIMENTS FOR CARRYING OUT THE INVENTION

Hereinafter, the embodiments of the present invention will be described in detail.

The cell-adhesive protein of the present invention is a cell-adhesive protein comprising methionine, which is characterized in that at least a portion of methionine residues is oxidized.

The degree of oxidation of the methionine residues is not particularly limited, as long as the effects of the present invention to improve cellular adhesiveness can be achieved. The oxidation degree is preferably 7% or more of, more preferably 10% or more of, further preferably 15% or more, still further preferably 20% or more, still further preferably 30% or more, still further preferably 40% or more, and particularly preferably 50% or more of the methionine residue.

Taking into consideration the balance between time and effort required for the oxidation process and the improvement of cellular adhesiveness, the oxidation degree of the methionine residue is preferably 7% to 50% of, more preferably 7% to 30% of, further preferably 7% to 15% of, and particularly preferably 7% to 10% of the methionine residue.

The treatment method for oxidizing the methionine residue is not particularly limited. For example, the methionine residue can be oxidized using a suitable oxidizing agent. Examples of the oxidizing agent used herein include hydrogen peroxide solution, sodium bromate, potassium bromate, sodium hypochlorite, potassium permanganate, and ozone. Among these, hydrogen peroxide solution is preferable.

The type of the cell-adhesive protein of the present invention is not particularly limited, as long as it comprises a methionine residue and has cellular adhesiveness. Specific examples of a protein having cellular adhesiveness include peptides having cell adhesion sequences (sequences indicated by single character code of amino acid, such as the sequence RGD, the sequence LDV, the sequence REDV (SEQ ID NO: 3), the sequence YIGSR (SEQ ID NO: 4), the sequence PDSGR (SEQ ID NO: 5), the sequence RYVVLPR (SEQ ID NO: 6), the sequence LGTIPG (SEQ ID NO: 7), the sequence RNIAEIIKDI (SEQ ID NO: 8), the sequence IKVAV (SEQ ID NO: 9), the sequence LRE, the sequence DGEA (SEQ ID NO: 10), and the sequence HAV). Other specific examples of a protein having cellular adhesiveness include gelatin-like proteins (e.g. gelatin, collagen, fibronectin, pronectin, or vitronectin) and laminin. These proteins may be either recombinant proteins or natural proteins. Specific examples of a recombinant protein include a recombinant gelatin, a recombinant fibronectin, a recombinant pronectin, a recombinant vitronectin, and a recombinant laminin. Among the above-described proteins, a recombinant gelatin is most preferable.

The recombinant gelatin is explained below.

The recombinant gelatin used in the present invention has repeats of a sequence represented by Gly-X-Y (wherein X and Y each independently represent any amino acid) that is characteristic to collagen (wherein a plurality of sequences Gly-X-Y may be identical to or different from one another).

Preferably, it comprises two or more sequences of cell adhesion signals in a single molecule thereof. As a recombinant gelatin used in the present invention, a recombinant gelatin having an amino acid sequence derived from a partial amino acid sequence of collagen can be used. Examples of a recombinant gelatin that can be used include, but are not limited to, recombinant gelatins described in EP1014176A2, U.S. Pat. No. 6,992,172, WO2004-85473, and WO2008/103041. A recombinant gelatin which is preferable as the recombinant gelatin used in the present invention is described below.

The recombinant gelatin used in the present invention has original properties of naturally occurring gelatin and thus it is highly biocompatible. In addition, the recombinant gelatin is not directly obtained from natural sources and thus has no risk of causing BSE or the like. In this regard, it has an excellent property of being non-infectious. In addition, the recombinant gelatin used in the present invention is more homogenous than naturally occurring gelatin. Further, the recombinant gelatin has a predetermined sequence. Thus, it is possible to precisely design the recombinant gelatin in terms of strength and degradability with few errors by crosslinking or the like described below.

The molecular weight of the recombinant gelatin used in the present invention is preferably 2 KDa to 100 KDa, more preferably 2.5 KDa to 95 KDa, further preferably 5 KDa to 90 KDa, and most preferably 10 KDa to 90 KDa.

Preferably, the recombinant gelatin contains repeats of a sequence represented by Gly-X-Y characteristic to collagen. Here, a plurality of sequences each represented by Gly-X-Y may be the same or different. Gly in Gly-X-Y represents glycine. X and Y in Gly-X-Y represent any amino acids (and preferably any amino acids other than glycine). When gelatin/collagen is compared with other proteins in terms of the amino acid composition or sequence, the GXY sequence is characteristic to collagen and forms a highly specific partial structure. Glycine accounts for approximately one-third of the partial structure as a whole. Glycine is repeatedly found in the amino acid sequence at a rate of 1 out of every 3 amino acids. Glycine is the simplest amino acid. There are few restrictions to arrangement of the molecular chain of glycine and thus glycine highly contributes to regeneration of the helix structure upon gelatinization. Preferably, an amino acid represented by X or Y is rich in imino acid (proline or oxyproline) and the imino acid accounts for 10% to 45% of the amino acid sequence as a whole. Amino acids forming the GXY repeat structure account for preferably 80% or more, more preferably 95% or more, and most preferably 99% or more of the amino acid sequence as a whole.

A generally available gelatin contains charged polar amino acids and uncharged polar amino acids at a ratio of 1:1. Here, the term "polar amino acid" specifically refers to cysteine, aspartic acid, glutamic acid, histidine, lysine, asparagine, glutamine, serine, threonine, tyrosine, or arginine. In particular, the term "uncharged polar amino acid" refers to cysteine, asparagine, glutamine, serine, threonine, or tyrosine. The percentage of polar amino acids relative to all amino acids constituting the recombinant gelatin used in the present invention is 10% to 40% and preferably 20% to 30%. In addition, the percentage of uncharged polar amino acids relative to the polar amino acids is preferably 5% to less than 20% and more preferably less than 10%. Preferably, the amino acid sequence does not contain one amino acid and preferably two amino acids or more selected from among serine, threonine, asparagine, tyrosine, and cysteine.

In general, it is known that a polypeptide contains a minimal amino acid sequence that functions as a cell adhesion signal sequence (e.g., "Pathophysiology" (*Byotai Seiri*) Vol. 9, No. 7(1990), p. 527, Nagai Shoten Co., Ltd.). It is preferable for a single molecule of the recombinant gelatin used in the present invention to have at least two cell adhesion signal sequences. In view of an increase in types of adhering cells, examples of such sequence are: preferably an RGD sequence, an LDV sequence, an REDV sequence (SEQ ID NO: 3), a YIGSR sequence (SEQ ID NO: 4), a PDSGR sequence (SEQ ID NO: 5), an RYVVLPR sequence (SEQ ID NO: 6), an LGTIPG sequence (SEQ ID NO: 7), an RNIAEIIKDI sequence (SEQ ID NO: 8), an IKVAV sequence (SEQ ID NO: 9), an LRE sequence, a DGEA sequence (SEQ ID NO: 10), and an HAV sequence (the amino acids are shown by one-letter notation), more preferably an RGD sequence, a YIGSR sequence (SEQ ID NO: 4), a PDSGR sequence (SEQ ID NO: 5), an LGTIPG sequence (SEQ ID NO: 7), an IKVAV sequence (SEQ ID NO: 9), and an HAV sequence; and particularly preferably an RGD sequence. Among the RGD sequence, an ERGD sequence (SEQ ID NO: 11) is preferred.

In terms of arrangement of RGD sequences in the recombinant gelatin used in the present invention, the number of amino acids present between two RGD sequences is preferably 0 to 100 and more preferably 25 to 60. Preferably, the number of amino acids is not uniformly determined.

In view of cell adhesion/growth, the number of such minimal amino acid sequences in a single protein molecule is preferably 3 to 50, more preferably 4 to 30, particularly preferably 5 to 20, and most preferably 12.

The percentage of RGD motifs to the total number of amino acids in the recombinant gelatin used in the present invention is preferably at least 0.4%. If the recombinant gelatin comprises 350 amino acids or more, each stretch of 350 amino acids contains preferably at least one RGD motif. The percentage of RGD motifs to the total number of amino acids is more preferably at least 0.6%, further preferably at least 0.8%, still further preferably at least 1.0%, even further preferably at least 1.2%, and most preferably at least 1.5%. The number of RGD motifs in the recombinant gelatin is preferably at least 4, more preferably 6, further preferably 8, and even further preferably 12 to 16 per 250 amino acids. A percentage of RGD motifs of 0.4% corresponds to at least one RGD sequence per 250 amino acids. The number of RGD motifs is represented by an integer. Therefore, in order to achieve a percentage of RGD motifs of 0.4%, it is necessary for a gelatin comprising 251 amino acids to contain at least two RGD sequences. Preferably, the recombinant gelatin of the present invention contains at least 2 RGD sequences per 250 amino acids, more preferably at least 3 RGD sequences per 250 amino acids, and further preferably at least 4 RGD sequences per 250 amino acids. In another embodiment, the recombinant gelatin of the present invention comprises at least 4, preferably 6, more preferably 8, and further preferably 12 to 16 RGD motifs.

In addition, the recombinant gelatin may be partially hydrolyzed.

Preferably, the recombinant gelatin used in the present invention has a structure comprising repeats of A-[(Gly-X-Y)n]m-B. Here, "m" is an integer of preferably 2 to 10 and more preferably 3 to 5. In addition, "n" is an integer of preferably 3 to 100, more preferably 15 to 70, and most preferably 50 to 65.

Preferably, a plurality of naturally occurring collagen sequence units are bound to form a repeat unit. The term "naturally occurring collagen" used herein may refer to any naturally occurring collagen. However, preferable examples thereof include type-I, type-II, type-III, type-IV, and type-V collagens. More preferably, type-I, type-II, and type-III collagens are used. In another embodiment, the origin of such collagen is preferably a human, bovine, pig, mouse, or rat and it is more preferably a human.

The isoelectric point of the recombinant gelatin used in the present invention is preferably 5 to 10, more preferably 6 to 10, and further preferably 7 to 9.5.

Preferably, the recombinant gelatin is not deaminated.

Preferably, the recombinant gelatin does not comprise telopeptide.

Preferably, the recombinant gelatin is a substantially pure collagen material prepared from a nucleic acid encoding a naturally occurring collagen.

Particularly preferably, the recombinant gelatin used in the present invention is a recombinant gelatin having the following (1) or (2):

(1) the amino acid sequence shown in SEQ ID NO: 1, or (2) an amino acid sequence having homology of 80% or more (more preferably 90% or more, and most preferably 95% or more) with the amino acid sequence shown in SEQ ID NO: 1 and having cellular adhesiveness.

The recombinant gelatin used in the present invention can be produced by a gene recombination technique known to persons skilled in the art. For instance, it can be produced according to the method described in EP1014176A2, U.S. Pat. No. 6,992,172, WO2004/85473, or WO2008/103041. Specifically, a transformant is produced by obtaining a gene encoding the amino acid sequence of a predetermined recombinant gelatin, incorporating the gene into an expression vector to prepare a recombinant expression vector, and introducing the vector into an appropriate host. The obtained transformant is cultured in an appropriate medium to produce a recombinant gelatin. Therefore, the recombinant gelatin used in the present invention can be prepared by collecting the produced recombinant gelatin from the culture product.

The recombinant gelatin used in the present invention may be cross-linked or may not be cross-linked, and is preferably cross-linked. Any method known in the art, such as thermal cross-linking, chemical cross-linking, cross-linking using an aldehyde (e.g., formaldehyde and glutaraldehyde), cross-linking using a condensing agent (carbodiimide, cyanamide, etc.), enzymatic cross-linking, photocrosslinking, UV cross-linking, hydrophobic interaction, hydrogen bond, or ionic interaction can be used as a cross-linking method. A cross-linking method using glutaraldehyde is most preferable.

Examples of the photocrosslinking include those based on light irradiation of a polymer containing a photoreactive group introduced therein, or light irradiation in the presence of a photosensitizer. Examples of the photoreactive group include a cinnamyl group, a coumarin group, a dithiocarbamyl group, a xanthene dye, and camphorquinone.

In the case of performing cross-linking using an enzyme, the enzyme is not particularly limited as long as it has the effect of cross-linking between the recombinant gelatins. The cross-linking can be performed using preferably transglutaminase and laccase, most preferably transglutaminase. Specific examples of proteins that may be subjected to enzymatic cross-linking with transglutaminase are not particularly limited as long as they are proteins having a lysine residue and a glutamine residue. The transglutaminase may be derived from a mammal or may be derived from a microbe. Specific examples thereof include ACTIVA series manufactured by Ajinomoto Co., Inc., mammal-derived transglutaminase sold as reagents, for example, guinea pig liver-derived transglutaminase, goat-derived transglutaminase, and rabbit-derived transglutaminase manufactured by Oriental Yeast Co., ltd., Upstate USA Inc., or Biodesign International, and human-derived blood coagulation factor (Factor XIIIa, Haematologic Technologies, Inc.).

The cross-linking of the recombinant gelatin involves two steps: a step of mixing a recombinant gelatin solution with a cross-linking agent and a step of reacting the resulting homogeneous solution.

In the present invention, the mixing temperature for the treatment of the recombinant gelatin with a cross-linking agent is not particularly limited as long as the solution can be mixed uniformly. The temperature is preferably 0° C. to 40° C., further preferably 0° C. to 30° C., further preferably 3° C. to 25° C., further preferably 3° C. to 15° C., further preferably 3° C. to 10° C., particularly preferably 3° C. to 7° C.

The temperature can be raised after the recombinant gelatin is mixed with the cross-linking agent. The reaction temperature is not particularly limited as long as the cross-linking proceeds. In consideration of the denaturation or degradation of the recombinant gelatin, the temperature is substantially 0° C. to 60° C., more preferably 0° C. to 40° C., further preferably 3° C. to 25° C., further preferably 3° C. to 15° C., further preferably 3° C. to 10° C., particularly preferably 3° C. to 7° C.

Since the above-described cell-adhesive protein of the present invention has high cellular adhesiveness, it is useful as a cell adhesion support. The cell adhesion support of the present invention can be used as a scaffolding base material or a therapeutic agent in regenerative medicine. The cell adhesion support of the present invention can be singly used as a therapeutic agent for regenerative medicine. The type of a disease is not limited, as long as it is a disease due to which tissues or organs need to be regenerated or newly generated.

The cell adhesion support of the present invention can be used as scaffolding for transplanting cells into a living body for the purpose of regenerative medicine. That is to say, the cell adhesion support of the present invention can be used as a regenerative medicine material. When the cell adhesion support of the present invention is used as a regenerative medicine material, cells may be dispersed on the cell adhesion support of the present invention, and the cell adhesion substrate containing the cells therein may be then transplanted into a living body. That is, the cell adhesion support of the present invention containing cells to be transplanted can be used as a regenerative medicine material. However, the intended use of the cell adhesion support of the present invention is not limited to regenerative medicine, and it can also be used for the culture of cells that is not for the purpose of transplantation.

Cells retained by the cell adhesion support of the present invention can be selected, as appropriate, depending on purpose. The type of cells is not particularly limited. Preferably, animal cells can be used, and in particular, human-derived cells can be used. The type of animal cells (in particular, human-derived cells) may be any of pluripotent cells, somatic stem cells, progenitor cells, and mature cells. Examples of the pluripotent cells that can be used herein include ES cells, GS cells, and iPS cells. Examples of the somatic stem cells that can be used herein include mesenchymal stem cells (MSC), hematopoietic stem cells, and neural stem cells. Examples of the progenitor cells and mature cells that can be used herein include cells derived from the skin, dermis, epidermis, muscle, cardiac muscle, nerve, bone, cartilage, endodermis, brain, epithelium, heart, kidney, liver, pancreas, spleen, oral cavity, cornea, or hair. Examples of the human-derived cells that can be used herein include ES cells, iPS cells, MSC, chondrocytes, osteoblasts, osteoprogenitor cells, mesenchyme cells, myoblasts, cardiac muscle cells, nerve cells, hepatic cells, beta cells, fibroblasts, corneal endothelial cells, vascular endothelial cells, corneal epithelial cells, and hematopoietic stem cells. For therapeutic purposes, either host-derived cells or transplantation cells obtained from the outside may be used. In addition, the origin of cells may be either autologous cells or allotransplanted cells.

When cells need to be seeded on the cell adhesion support of the present invention, seeding of the cells may be carried out according to an ordinary method. Cells may be seeded in the form of a cell suspension onto the cell adhesion support of the present invention placed in a suitable vessel.

Hereinafter, the present invention will be more specifically described in the following examples. However, these examples are not intended to limit the scope of the present invention.

EXAMPLES

Example 1

Recombinant Gelatin

As a recombinant gelatin, the following CBE3 (described in WO2008-103041) was prepared.
CBE3
Molecular weight: 51.6 kD
Structure: Gly-Ala-Pro[(Gly-X-Y)$_{63}$]$_3$Gly
Number of amino acids: 571
Number of RGD sequences: 12
Imino acid content: 33%
Substantially 100% of amino acids form the Gly-X-Y repeat structure.
The amino acid sequence of CBE3 does not contain any of serine, threonine, asparagine, tyrosine, and cysteine.
CBE3 has an ERGD sequence.
Isoelectric point: 9.34
Amino acid sequence (SEQ ID NO: 1 in the Sequence Listing) (This amino acid sequence corresponds to the amino acid sequence shown in SEQ ID NO: 3 in WO2008/103041. Note that "X" at the end was modified to "P.")

GAP (GAPGLQGAPGLQGMPGERGAAGLPGPKGERGDAGPKGADGAPGAP

GLQGMPGERGAAGLPGPKGERGDAGPKGADGAPGKDGVRGLAGPIGPPG

ERGAAGLPGPKGERGDAGPKGADGAPGKDGVRGLAGPIGPPGPAGAPGA

PGLQGMPGERGAAGLPGPKGERGDAGPKGADGAPGKDGVRGLAGPP) 3G

In the Examples described below, the above CBE3 was used as a recombinant gelatin.
(1) Production of Oxidized Recombinant Gelatin
In order to produce an oxidized recombinant gelatin, the above-mentioned CBE3 was treated with a hydrogen peroxide solution for 2 hours. Thereafter, in order to confirm oxidation of methionine contained in the thus produced sample, an amino acid composition analysis was performed. As a comparative control, CBE3 (fresh recombinant gelatin) that had not been left for any length of time was used. The implementation of this test was outsourced to Toray Research Center. Specifically, a recombinant gelatin was hydrolyzed with 6 M hydrochloric acid, and quantification was then carried out on the resultant according to a ninhydrine method using an amino acid analyzer (L-8500, Hitachi, Ltd.). The oxidation rate of methionine contained in each of the oxidized recombinant gelatin and the fresh recombinant gelatin is shown in Table 1 below.

TABLE 1

Oxidation rate of recombinant gelatin

| Sample | Methionine oxidation rate per molecule of recombinant gelatin |
|---|---|
| Oxidized recombinant gelatin | 7% |
| Fresh recombinant gelatin | 6% |

(2) Cell Adhesion Test
Coating with Recombinant Gelatin
First, the oxidized recombinant gelatin and the fresh recombinant gelatin were each dissolved in PBS (Invitrogen), and a solution containing 0.005 µg/ml the recombinant gelatin was prepared. 64 µl of the prepared solution was added to a 96-well plate (BD Falcon), and it was then incubated at 37° C. for 2 hours. Thereafter, the resultant was washed with PBS twice. Given that the total amount of the coated recombinant gelatin was adsorbed on the plate, the number of oxidized methionine residues in the oxidized recombinant gelatin was larger than that in the fresh recombinant gelatin by approximately $1 \times 10^9$ residues.
Cell Seeding
Vero cells were cultured in an MEM medium (Invitrogen) containing 10% FBS (Invitrogen). Once the cells had become subconfluent, they were removed using 0.25% trypsin-EDTA (Invitrogen), and a medium was then added thereto, followed by centrifugation. The resulting cells were washed with a serum-free medium once. Thereafter, a cell suspension was prepared, and the cell density thereof was adjusted to be $1 \times 10^5$ cells/ml. Then, 100 µl each of the cells was seeded on the previously prepared 96-well plate.
Evaluation of Cellular Adhesiveness
The cells were left at rest at 37° C. in an incubator for 1 hour. Subsequently, the medium was removed, and the cells were then washed twice with PBS that had been heated to 37° C. The resultant was used for evaluation of cellular adhesiveness.

The number of cells adhered was evaluated using Quant-iT™ PicoGreen Kit (Invitrogen). The evaluation was basically carried out according to an experimental method recommended by the manufacturer of this kit. The experimental method will be described below.

100 µl of 0.2% Triton-X solution was added to each well onto which the cells had been seeded. Thereafter, the cells were completely dissolved in the solution by freeze/thaw actions. A PicoGreen reagent was diluted with a TE buffer, and 100 µl of the diluted solution was added to each well, followed by being stirred with a shaker. Thereafter, measurement was carried out at an excitation wavelength of 485 nm and an emission wavelength of 535 nm.
Cellular Adhesiveness
As a result of the cellular adhesiveness test, the plate coated with the oxidized RCP had higher adhesiveness than that of the plate coated with the fresh recombinant gelatin (FIG. 1). Therefore, it was confirmed that the oxidized recombinant gelatin improves cellular adhesiveness by factors other than cell adhesion sequence.

The invention claimed is:

1. A cell-adhesive protein comprising methionine, wherein at least a portion of methionine residues is oxidized;
wherein said cell-adhesive protein is a gelatin-like protein and wherein the gelatin-like protein is a recombinant gelatin having an amino acid sequence derived from a partial amino acid sequence of collagen; and
wherein the amino acid sequence of the recombinant gelatin does not comprise any of serine and threonine.

2. The cell-adhesive protein according to claim 1, wherein 7% or more of the methionine residues in the protein is oxidized.

3. The cell-adhesive protein according to claim claim 1, wherein at least a portion of the methionine residues is oxidized by an oxidizing agent.

4. The cell-adhesive protein according to claim 1, the cellular adhesiveness of which is improved by oxidization of the methionine residue.

5. The cell-adhesive protein according to claim 1, wherein the recombinant gelatin has repeats of a sequence represented by Gly-X-Y, wherein X and Y each independently represent any amino acid, that is characteristic to collagen, wherein a plurality of sequences Gly-X-Y may be identical to or different from one another, and has a molecular weight of 2 KDa or more and 100 KDa or less.

6. The cell-adhesive protein according to claim 1, wherein the recombinant gelatin has repeats of a sequence represented by Gly-X-Y, wherein X and Y each independently represent any amino acid, that is characteristic to collagen, wherein a plurality of sequences Gly-X-Y may be identical to or different from one another, and has a molecular weight of 10 KDa or more and 90 KDa or less.

7. The cell-adhesive protein according to claim 1, wherein the recombinant gelatin has repeats of a sequence represented by Gly-X-Y, wherein X and Y each independently represent any amino acid, that is characteristic to collagen, wherein a plurality of sequences Gly-X-Y may be identical to or different from one another, and comprises two or more sequences of cell adhesion signals in a single molecule thereof.

8. The cell-adhesive protein according to claim 7, wherein the cell adhesion signal is an amino acid sequence represented by Arg-Gly-Asp.

9. The cell-adhesive protein according to claim 1, wherein the recombinant gelatin is cross-linked.

10. The cell-adhesive protein according to claim 9, wherein the cross-linking is carried out with an aldehyde, a condensing agent, thermal cross-linking, photocrosslinking, or an enzyme.

11. A cell-adhesive protein comprising methionine, wherein at least a portion of methionine residues is oxidized;
wherein said cell-adhesive protein is a gelatin-like protein and wherein the gelatin-like protein is a recombinant gelatin having an amino acid sequence derived from a partial amino acid sequence of collagen; and
wherein the amino acid sequence of the recombinant gelatin does not comprise an amino acid sequence represented by Asp-Arg-Gly-Asp.

12. A cell-adhesive protein comprising methionine, wherein at least a portion of methionine residues is oxidized;
wherein said cell-adhesive protein is a gelatin-like protein and wherein the gelatin-like protein is a recombinant gelatin having an amino acid sequence derived from a partial amino acid sequence of collagen; and
wherein the recombinant gelatin is represented by the following formula:

$$A\text{-}[(Gly\text{-}X\text{-}Y)_n]_m\text{-}B$$

wherein A represents any given amino acid or amino acid sequence, B represents any given amino acid or amino acid sequence, an n number of X each independently represent any amino acid, an n number of Y each independently represent any amino acid, n represents an integer of 3 to 100, m represents an integer of 2 to 10, and an n number of Gly-X-Y may be identical to or different from one another.

13. The cell-adhesive protein according to claim 12, wherein the recombinant gelatin is represented by the following formula:

$$Gly\text{-}Ala\text{-}Pro\text{-}[(Gly\text{-}X\text{-}Y)_{63}]_3\text{-}Gly$$

wherein 63 X each independently represent any amino acid, 63 Y each independently represent any amino acid, and an n number of Gly-X-Y may be identical to or different from one another.

14. A cell-adhesive protein comprising methionine, wherein at least a portion of methionine residues is oxidized;
wherein said cell-adhesive protein is a gelatin-like protein and wherein the gelatin-like protein is a recombinant gelatin having an amino acid sequence derived from a partial amino acid sequence of collagen; and
wherein the recombinant gelatin has (1) the amino acid sequence shown in SEQ ID NO: 1, or (2) an amino acid sequence having homology of 80% or more with the amino acid sequence shown in SEQ ID NO: 1 and having cellular adhesiveness.

15. A cell adhesion support comprising the cell-adhesive protein according to claim 1.

16. A method for producing the cell-adhesive protein according to claim 1, which comprises treating a cell-adhesive protein comprising methionine with an oxidizing agent.

* * * * *